US006469171B1

(12) United States Patent
Banwell et al.

(10) Patent No.: US 6,469,171 B1
(45) Date of Patent: Oct. 22, 2002

(54) SYNTHESES OF A VARIETY OF LAMELLARIN COMPOUNDS AND ANALOGUES

(75) Inventors: Martin Gerhardt Banwell, Aranda (AU); Bernard Luke Flynn, Griffith (AU)

(73) Assignee: The Australian National University, Acton Australian Capital Territory (AU)

( * ) Notice: Subject to any disclaimer, the term of this patent is extended or adjusted under 35 U.S.C. 154(b) by 0 days.

(21) Appl. No.: 09/720,320

(22) PCT Filed: Jun. 25, 1999

(86) PCT No.: PCT/AU99/00516

§ 371 (c)(1),
(2), (4) Date: Feb. 2, 2001

(87) PCT Pub. No.: WO99/67250

PCT Pub. Date: Dec. 29, 1999

(30) Foreign Application Priority Data

Jun. 25, 1998 (AU) ............................................. 4333/98

(51) Int. Cl.$^7$ ........................................... C07D 471/00
(52) U.S. Cl. .............................. 546/49; 546/56; 546/81; 546/84; 546/113; 548/418; 548/427; 548/430; 548/432; 548/532
(58) Field of Search ............................... 548/532, 418, 548/427, 430, 432; 546/84, 113, 49, 56, 81

(56) References Cited

U.S. PATENT DOCUMENTS

| 3,407,199 | A | * | 10/1968 | Pachter | |
| 3,963,480 | A | | 6/1976 | Bailey | ........................... 71/95 |
| 4,046,775 | A | | 9/1977 | Bailey et al. | ............. 260/326.2 |

FOREIGN PATENT DOCUMENTS

| FR | 1175921 | 1/1970 | ........... C07D/99/02 |
| FR | 1592066 | 6/1970 | |
| WO | WO 97/01336 | 1/1997 | ......... A61K/31/435 |
| WO | WO 98/50365 | 11/1998 | ......... C07D/217/20 |
| WO | WO 99/67250 | 12/1999 | ......... C07D/491/14 |

OTHER PUBLICATIONS

J. Am Chem. Soc. 1999, 121(1) 54–62 (Dec. 19, 1998).*
Anderson, R.J. et al., (1985), "Metabolites of the Marine Prosobranch Mollusc *Lamellaria sp.*," *J. Am. Chem. Soc.* 107:5492–5495.
Antonio, Y. et al., (1994), "Oxidative radical cyclization to pyrroles under reducing conditions. Reductive desulfonylation of α–sulfonylpyrroles with tri–n–butyltin hydride$^{1,2}$," *Can. J. Chem.* 72:15–22.
Bailey, D.M. et al., (1971), "Ethyl Pyrrole–2 Carboxylate," *Org. Synth.* 51:100–102.

Banwell, M.G. et al., (1997), "Convergent syntheses of the pyrrolic marine natural products lamellarin–O, lamellarin–O, lukianol–A and some more highly oxygenated congeners," *Chem. Commun.* 2:207–208.
Banwell, M.G. et al., (1997), "Convergent total synthesis of lamellarin K," *Chem. Commun.* 2:2259–2260.
Banwell, M.G. et al., (Nov. 1998), "Selective Cleavage of Isopropyl Aryl Ethers by Aluminum Trichloride," *J. Org. Chem.* 63:9139–9144.
Bélanger, P. (1979), "Electrophilic Substitutions on 2–Trichloroacetylpyrrole," *Tetrahedron Lett.* #27 pp. 2505–2508.
Black, D. St.C. et al., (1989), "A Direct Synthesis of Pyrrolophenanthridone Alkaloids," *Tetra. Lett.* 30(42):5807–5808.
Boger, D.L. et al., (Jan. 1999), "Total Syntheses of Ningalin A, Lamellarin O, Lukianol A, and Permethyl Storniamide A Utilizing Heterocyclic Azadiene Diels–Alder Reactions," *J. Am. Chem. Soc.* 121:54–62.
Brimble, M.A. et al., (1988), "Synthesis of 2–Methylpyrrolo [1,2–α]pyrazine–1(2H)–one," *Aust. J. Chem.* 41(10):1583–1590.
Burwood, M. et al., (1995), "Sequential and Cascade [2 +2]–Cycloaddition–Palladium Catalysed Cyclisation: Bicyclic β–Lactams," *Tetra. Lett.* 36(49):9053–9056.

(List continued on next page.)

*Primary Examiner*—Alan L. Rotman
*Assistant Examiner*—Raymond Covington
(74) *Attorney, Agent, or Firm*—Greenlee, Winner and Sullivan, P.C.

(57) ABSTRACT

The present invention relates to methods for preparing a variety of Lamellarin compounds and analogues via a synthetic intermediate, which methods involved the step of performing an intramolecular cyclization of a compound of Formula (I) to produce compounds of Formula(II), wherein the variables are given in the specification.

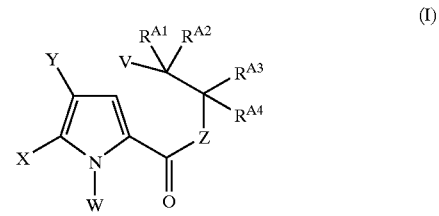

(I)

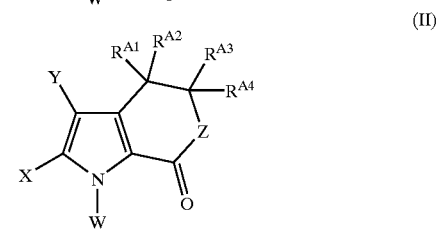

(II)

28 Claims, No Drawings

OTHER PUBLICATIONS

Carroll, A.R. et al., (1993), "Studies of Australian Ascidians. I Six New Lamellarin–Class Alkanoids from a Colonial Ascidian, Didemnum sp.," Aust. J. Chem. 46:489–501.
Chemical Abstract 130:282331, Konig Burkhard (1999) "Synthesis of an Fmoc N–methyl 1H–pyrrole amino acid pentafluoro–phenol ester."
Chemical Abstract 129:302520, Gong, Yang (1998) "Synthesis of indolizine amide derivatives."
Chemical Abstract 129:41035, Ito, Takatoshi (1998) "Preparation and use of novel (s)–beta–chlorodifluoromethyl–beta–propiolactone as a chiral fluroinated building block."
Chemical Abstract 126:277429, Di Santo, R. (1997) "Anti–fungal estrogen–like imidazoles, Synthesis and anti–fungal activities of thienyl and 1H–pyrrolyl derivatives of 1–aryl–2–(1H–imidazol–1–yl) ethane."
Chemical Abstract 126:263906, Fujisawa, Tamotsu (1997) "Facile synthesis of (s)–beta–trichloromethyl aromatic ketones by the regiosleective ring cleavage of chiral beta–trichloromethyl–beta–propiolactone under Friedel–Crafts conditions."
Chemical Abstract 112:7428, Uchida, Minoru (1989) "Studies on gastric antiulcer active agents. III. Synthesis of 1–substituted 4–(5–tetrazolyl)thio–1–butanones and related compounds."
Chemical Abstract 110:213158, Murakami, Yasuoki (1988) "Synthetic study of indoles and related compounds, Part XIX. A new synthesis of eupolauramine from a benz[f]indole derivative."
Chemical Abstract 81:63432, Vecchietti, Vittorio (1974) "Nitropyrrole derivatives with antimicrobial activity."
Chemical Abstract 80:422, Bailey, Denis M. (1973) "Pyrrole antibacterial agents II. 4,5–Dihalopyrrole–2–carboxylic acid derivatives."
Chemical Abstract 75:129595, Cooper, Graham Hamilton (1971) "Cyclopropyl 2–pyrrolyl ketone."
Davis, R.A. et al., (Mar. 1999), "New Lamellarin Alkanoids from the Australian Ascidian, Didemnum chartaceum," J. Nat. Prod. 62:419–424.
Desarbre, E. and Mérour, J., (1995), "Heck Annulation on 2–Position of Indoles or 1H–Pyrrolo[2,3–b]Pyridine," Heterocycles 41(9):1987–1998.
Fujisawa, T. et al., (Jan. 1997), "Facile Synthesis of (S)–β–Hydroxy–β–trichloromethylated Aromatic Ketones by the Regioselective Ring Cleavage of Chiral β–Trichloromethyl–β–propiolactone Under the Friedel––Crafts Conditions," Tetra. Lett. 38(9):1593–1596.
Grigg, R. et al., (1994) "Palladium Catalysed Synthesis of Spiroindolines," Tetrahedron 50(2):359–370.
Harbuck, J.W. and Rapoport, H.. (1972), "Facile Introduction of Ester Groups into the Pyrrole Nucleus via Trichloroacetylation and Alcoholysis[1]," J. Org. Chem. 37(23):3618–3622.

Harayama, T. et al., (Oct. 1997), "Internal Aryl–Aryl Coupling Reaction Using a Novel and Highly Active Palladium Reagent Prepared From Pd(OAc)$_2$, DPPP, and Bu$_3$P," Chem. Pharm. Bull. 45(10):1723–1725.
Heim, A. et al., (1997) "Biomimetic Synthesis of Lamellarin G Trimethyl Ether," Angew. Chem. Int. Ed. Engl. 36(½):155–156.
Hermann, W.A. et al., (1997), "Palladacycles: Efficient New Catalysts for the Heck Vinylation Of Aryl Halides," Chem. Eur. J. 3(8):1357–1364.
Ishibashi, F. et al., (1997), "Total Synthesis of Lamellarin D and H. The First Synthesis of Lamellarin–Class Marine Alkenoids," Tetrahedron 53(17):5951–5962.
Ito, et al., (1998), "Preparation of Use of Novel (S)–β–Chlorodifluoromethyl–β–propiolactone as a Chiral Fluorinated Building Block," Tetrahedron 54:5523–5530.
Kita, Y. et al., (1996), "Non–phenolic oxidative coupling of phenol ether derivatves using phenyliodine(III) bis(trifluoroacetate)," Chem. Commun. Pp. 1481–1482.
Lindquist, N. and Fenical, W., (1988), "New Alkanoids of the Lamellarin Class from the Marine Ascidian Didemnum chartaceum (Sluiter, 1909)," J. Org. Chem. 53:4570–4574.
Minguez, J.M. et al., (1996), "Pyrrolodiazines. 2. Structure and Chemistry of Pyrrolo[1,2–α]pyrazine and 1,3–Dipolar Cycloaddition of Its Azomethine Ylides," J. Org. Chem. 61:4655–4665.
Minguez, J.M. et al., (1997), "Pyrrolodiazines, 4. Structure and Chemistry of 3,4–Dihydropyrrolo[1,2–α]pyrazine," Tetrahedron 53(27):9341–9356.
Moody, C.J. and Norton, C.L., (1995), "Synthesis of 1,2–Fused Indoles by Radical Cyclisation," J. Org. Chem 36:9051–9052.
Quesada, A.R. et al., (1996), "Polyaromatic alkanoids from marine invertebrates as cytotoxic compounds and inhibitors of multidrug resistance caused by P–glycoprotein," British Journal of Cancer 74:677–682.
Reddy, M.V.R. and Faulkner, D.J., (1997), "New Lamellarin Alkaloids from an Unidentified Ascidian from the Arabian Sea," Tetrahedron 53(10):3457–3466.
Reddy, M.V.R. et al., (Jun. 1999), "Lamellarin α 20–Sulfate, and Inhibitor of HIV–1 Integrase Active against HIV–1 Virus in Cell Culture," J. Med. Chem. 42:1901–1907.
Toyota, M. et al., (1994), "An Efficient Synthesis of 1,2,3,4–Tetra–Substituted Pyrroles Via Intramolecular Azomethine Ylide [3+2] Dipolar Cycloaddition," Heterocycles 39(1):39–42.
Vedejs, and Piotrowski, D.W., (1993), "Oxazole Activation for Axomethine Ylide Trapping: Singly and Doubly Tethered Substrates," J. Org. Chem. 58:1341–1348.
Wallace, D.M. et al., (1993), "Rational Tetraarylporphyrin Syntheses: Tetraarylporphyrins from the MacDonald Route," J. Org. Chem. 58:7245–7257.

* cited by examiner

SYNTHESES OF A VARIETY OF LAMELLARIN COMPOUNDS AND ANALOGUES

TECHNICAL FIELD

The present invention is generally directed to intermediates useful in the preparation of compounds useful in therapy. More specifically, the present invention relates to intermediates useful in the preparation of a class of fused polycyclic alkaloids. The invention also relates to methods for the preparation of the fused polycyclic alkaloids and their analogues and derivatives.

BACKGROUND ART

Naturally occurring molecules which exhibit potentially beneficial pharmacological properties are isolable from a range of environments, such as marine, plant and microbial sources. One example of such molecules is the general class of compounds known as the Lamellarins. These polyaromatic alkaloids are, isolated from marine sources and comprise a fused framework. Lamellarins C and D have been shown to cause inhibition of cell division in fertilised sea urchin assay, whereas Lamellarins I, K and L all exhibit comparable and significant cytotoxicity against P388 and A549 cell lines in culture. Recently, Lamellarin N has been shown to exhibit activity in lung cancer cell lines by acting as a Type IV microtubule poison. Furthermore, these compounds have also been shown to possess cytotoxic activity on multidrug resistant cells as well as efficacy as non-toxic modulators of the multidrug resistant phenotype and, therefore, afford an attractive potential source of chemotherapeutic agents.

However, the potential clinical usefulness of the Lamellanins is severely limited by the modest quantities produced naturally as well as the difficulties involved in their isolation.

There has accordingly, been significant activity directed towards the development of a synthetic route to this class of molecules, and approaches to these molecules have included a sequential double cyclization of a 1,3,4-triaryl-2,5-dicarboxysubstituted pyrrole ring (Steglich et al, *Angew., Chem. Int. Ed. Eng.* 1997, 36, 155), and N-ylide-mediated pyrrole ring formation to install the pyrrole and lactone portions of the molecule (Banwell et al, *Chem. Commun.,* 1997, 2259) Ishibashi et al, *Tetrahedron,* 1997, 53, 5951).

The present invention now provides an alternative method via a synthetic intermediate, which allows for the incorporation of a range of substitution patterns and potentially permits access to a variety of Lamellarin compounds and analogues containing the fused polycyclic-pyrrole core.

DISCLOSURE OF THE INVENTION

Accordingly, in a first aspect the invention relates to a method for the preparation of a compound of Formula (II).

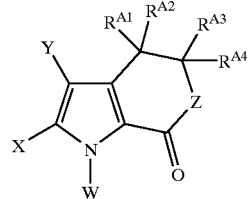

comprising the step performing an intramolecular cyclization of a compound of Formula (I):

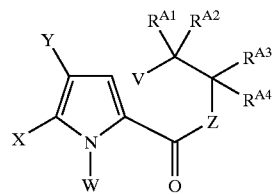

wherein:
$R^{A1-A4}$ are each independently selected from hydrogen, optionally substituted alkyl optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano; or $R^{A2}$ and $R^{A3}$ may optionally together form a bond and $R^{A1}$ and $R^{A4}$ are as defined above or together with the carbon atoms to which they are attached form an optionally substituted carbocyclic or heterocyclic group; or $R^{A2}$ and $R^{A3}$, together with the carbon atoms to which they are attached form an optionally substituted saturated or unsaturated carbocyclic or heterocyclic group; or $R^{A1}R^{A2}C-CR^{A3}R^{A4}$ forms an optionally substituted aryl group or aromatic heterocyclic group;

Y is selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano;

W and X are as defined for Y, or together with the nitrogen and carbon atoms to which they are attached, form a saturated or unsaturated nitrogen containing heterocyclic group which may be optionally substituted or optionally fused to a saturated or unsaturated carbocyclic group, aryl group or heterocyclic group;

V represents a halogen or hydrogen atom;

Z is $-(CH_2)_n-U-(CH_2)_o-$ where U is selected from $CH_2$, NH or a heteroatom, and n and o are independently selected from 0, 1, 2 or 3.

In a second aspect, the present invention provides an intermediate compound useful in the preparation of compounds of Formula (II), wherein said intermediate is of Formula (I):

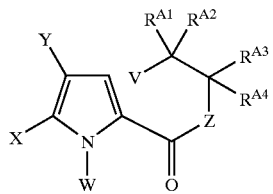

(I)

wherein:
  $R^{A1-A4}$ are each independently selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano; or
  $R^{A2}$ and $R^{A3}$ may optionally together form a bond and $R^{A1}$ and $R^{A4}$ are as defined above or together with the carbon atoms to which they are attached form an optionally substituted carbocyclic or heterocyclic group; or
  $R^{A2}$ and $R^{A3}$, together with the carbon atoms to which they are attached form an optionally substituted saturated or unsaturated carbocyclic or heterocyclic group; or
  $R^{A1}R^{A2}C-CR^{A3}R^{A4}$ forms an optionally substituted aryl group or aromatic heterocyclic group;
  Y is selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano;
  W and X are as defined for Y, or together with the nitrogen and carbon atoms to which they are attached, form a saturated or unsaturated nitrogen containing heterocyclic group which may be optionally substituted or optionally fused to a saturated or unsaturated carbocyclic group, aryl group or heterocyclic group;
  V represents a halogen or hydrogen atom;
  Z is —(CH$_2$)$_n$—U—(CH$_2$)$_o$— where U is selected from CH$_2$, NH or a heteroatom, and n and o are independently selected from 0, 1, 2 or 3.

Yet a further aspect of the present invention relates to compounds of Formula (II) as defined above, prepared by the methods described herein.

As used herein the term "alkyl", denotes straight chain, branched or cyclic fully saturated hydrocarbon residues. Unless the number of carbon atoms is specified the term preferably refers to C$_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

As used herein the term "alkenyl" denotes groups formed from straight chain, branched or cyclic hydrocarbon residues containing at least one carbon-carbon double bond including ethylenically mono-, di- or poly-unsaturated alkyl or cycloalkyl groups as previously defined. Unless the number of carbon atoms is specified the term preferably refers to C$_{1-20}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

As used herein the term "alkynyl" denotes groups formed from straight chain, branched or cyclic hydrocarbon residues containing at least one carbon-carbon triple bond including ethynically mono-, di- or poly- unsaturated alkyl or cycloalkyl groups as previously defined. Unless the number of carbon atoms is specified the term preferably refers to C$_{1-20}$ alkynyl. Examples include ethynyl, 1-propynyl, 2-propynyl, and butynyl isomers, and pentynyl isomers.

The terms "alkoxy, "alkenoxy and "alkynoxy respectively denote alkyl, alkenyl and alkynyl groups as hereinbefore defined when linked by oxygen.

The term "halogen" denotes fluorine, chlorine, bromine or iodine.

The term "aryl" denotes single, polynuclear, conjugated and fused residues of aromatic hydrocarbon ring systems. Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl.

The term "heterocyclic" denotes mono- or polycarbocyclic groups, including aryl, wherein at least one carbon atom is replaced by a heteroatom, preferably selected from nitrogen, sulphur and oxygen. Where the mono- or polycarbocyclic group which has at least one carbon atom replaced by a heteroatom is an aryl group, this is referred to as a aromatic heterocyclic group.

Suitable heterocyclic groups include N-containing heterocyclic groups, such as, unsaturated 3 to 6 membered heteromonocyclic groups containing 1 to 4 nitrogen atoms, for example, pyrrolyl, pyrrolinyl, imidazolyl, imidazolinyl, pyrazolyl, pyridyl, pyrimidinyl, pyrazinyl, pyridazinyl, triazolyl or tetrazolyl;

saturated 3 to 6-membered heteromonocyclic groups containing 1 to 4 nitrogen atoms, such as, pyrrolidinyl, imidazolidinyl, piperidyl, pyrazolidinyl- or piperazinyl;

condensed saturated or unsaturated heterocyclic groups containing 1 to 5 nitrogen atoms, such as, indolyl, isoindolyl, indolinyl, isoindolinyl, indolizinyl, isoindolizinyl, benzimidazolyl, quinolyl, isoquinolyl, indazolyl, benzotriazolyl, purinyl, quinazolinyl, quinoxalinyl, phenanthradinyl, phenathrolinyl, phthalazinyl, naphthyridinyl, cinnolinyl, pteridinyl, perimidinyl or tetrazolopyridazinyl;

saturated 3 to 6-membered heteromonocyclic groups containing 1 to 3 oxygen atoms, such as tetrahydrofuranyl, tetrahydropyranyl, tetrahydrodioxinyl, unsaturated 3 to 6-membered hetermonocyclic group containing an oxygen atom, such as, pyranyl, dioxinyl or furyl;

condensed saturated or unsaturated heterocyclic groups containing 1 to 3 oxygen atoms, such as benzofuranyl, chromenyl or xanthenyl;

unsaturated 3 to 6-membered heteromonocyclic group containing 1 to 2 sulphur atoms, such as, thienyl or dithiolyl;

unsaturated 3 to 6-membered heteromonocyclic group containing 1 to 2 oxygen atoms and 1 to 3 nitrogen atoms, such as, oxazolyl, oxazolinyl, isoxazolyl, furazanyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl, thiazolinyl or thiadiazoyl;

saturated 3 to 6-membered heteromonocyclic group containing 1 to 2 sulphur atoms and 1 to 3 nitrogen atoms, such as, thiazolidinyl; and unsaturated condensed heterocyclic group containing 1 to 2 sulphur atoms and 1 to 3 nitrogen atoms, such as, benzothiazolyl or benzothiadiazolyl.

The term "acyl" refers to a carboxylic acid residue wherein the OH is replaced with a residue, for example, as defined for W, X, and Y and specifically may denote carbamoyl, aliphatic acyl group or acyl group containing an aromatic ring, which is referred to as aromatic acyl or a heterocyclic ring, which is referred to as heterocyclic acyl, preferably $C_{1-20}$ acyl. Examples of suitable acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

The term "acyloxy" refers to acyl, as herein before defined, when linked by oxygen.

In this specification "optionally substituted" is taken to mean that a group may or may not be further substituted or fused (so as to form a condensed polycyclic group) with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy mercapto, alkylthio, benzylthio, acylthio, cyano, nitro, sulfate and phosphate groups. The term "optionally protected" is taken to mean that a group such as a hydroxy group may or may not be protected by a protecting group. Suitable protecting groups are known and examples thereof are described in *Protective Groups in Organic Synthesis*, by T. W. Greene, (1981), John Wiley & Son.

As used herein, "heteroatom" refers to any atom other than a carbon atom which may be a member of a cyclic organic compound. Examples of suitable heteroatoms include nitrogen, oxygen, sulfur, phosphorous, boron, silicon, arsenic, sellenium and telluruim, especially nitrogen, oxygen and sulfur.

In preferred embodiments of compounds of Formulae (I) and (II), U, as defined in Z, is selected from one of $CH_2$, NH, oxygen or sulfur. More preferably U is NH or oxygen. Most preferably, U is oxygen. In another preferred embodiment of Z, n+o=0, 1, 2, 3 or 4. Suitable examples of Z include —O—$CH_2$—, —$CH_2$—N—, —O—$CH_2$—O—, —$(CH_2)_3$—, —$CH_2$—NH—$CH_2$— or —$CH_2$—O—$CH_2$—. In another preferred embodiment, n and o are both zero.

In another preferred form, V is hydrogen, iodine or bromine.

In other embodiments of Formulae (I) and (II), when W and X, together with the nitrogen and carbon atoms to which they are attached, form a saturated or unsaturated heterocyclic group, the group is preferably optionally substituted quinolinyl, optionally substituted isoquinolinyl, optionally substituted dihydroquinolinyl, optionally substituted dihydroisoquinolinyl, optionally substituted pyridyl or dihydro or tetrahydro congeners thereof, or optionally substituted phenanthridine. Preferably, W and X together with the nitrogen and carbon atoms to which they are attached, form an optionally substituted isoquinolinyl or optionally substituted dihydroisoquinolinyl group of general Formula (i):

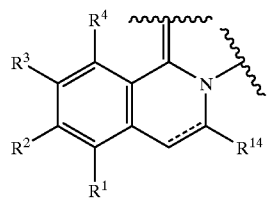

(i)

wherein $R^1$–$R^4$ and $R^{14}$ are as defined for Y above, and ══ represents an optional double bond.

Preferably $R^1$–$R^4$ of Formula (i) are hydrogen; hydroxy; optionally substituted alkyl; optionally substituted alkyloxy; acyloxy; carboxy; carboxy ester, wherein the ester is preferably methyl, ethyl, propyl or butyl ester; optionally substituted amino,; carboxamido, wherein the nitrogen atom thereof is optionally substituted by one or two alkyl groups independently selected from methyl, ethyl, propyl or butyl; or sulfate. Most preferably they are hydrogen, hydroxy, methoxy, ethoxy, iso-propoxy, methyl, ethyl, propyl, acetoxy or sulfate. Preferably $R^{14}$ is hydrogen or hydroxy.

In yet other embodiments of Compounds of Formulae (I) and (II), when $R^{A1}R^{A2}C$—$CR^{A3}R^{A4}$ form an aryl group or an aromatic heterocyclic group, it may be an optionally substituted benzene or naphthalene ring or an optionally substituted aromatic heterocyclic group such as pyridine, furan, pyrrole or thiophene and benzene-fused analogues thereof, for example, quinoline, indole, benzofuran and benzothiophene. Attachment of the bicyclic heterocyclic group may be via the benzene or heterocyclic ring. Preferably $R^{A1}R^{A2}C$—$CR^{A3}R^{A4}$ forms an optionally substituted benzene group. Preferably the substituents are hydrogen; hydroxy; optionally substituted alkyl; optionally substituted alkyloxy; acyloxy; carboxy; carboxy ester, wherein the ester is preferably methyl, ethyl, propyl or butyl ester; optionally substituted amino,; carboxamido, wherein the nitrogen atom thereof is optionally substituted by one or two alkyl groups independently selected from methyl, ethyl, propyl or butyl; or sulfate. Most preferably they are hydrogen, hydroxy, methoxy, ethoxy, iso-propoxy, methyl, ethyl, propyl, acetoxy or sulfate.

In another embodiment $R^{A1-A4}$ are preferably independently selected from hydrogen, optionally substituted alkyl, optionally protected hydroxy, optionally substituted alkoxy, optionally substituted phenyl or acyloxy. In one preferred embodiment, at least one of $R^{A1}$ or $R^{A3}$ may be hydrogen. In another embodiment, both $R^{A1}$ and $R^{A3}$ are hydrogen. In yet a further embodiment, three or four of $R^{A1-A4}$ are hydrogen.

In another embodiment, when $R^{A2}$ and $R^{A3}$ together form a bond so as to form a group $R^{A1}C$=$CR^{A4}$, $R^{A1}$ and $R^{A4}$ each may be independently selected from hydrogen; hydroxy; optionally substituted alkyl; optionally substituted alkyloxy; acyloxy; carboxy; carboxy ester, wherein the ester is preferably methyl, ethyl, propyl or butyl ester; optionally substituted amin or; carboxamido, wherein the nitrogen atom thereof is optionally substituted by one or two alkyl groups independently selected from methyl, ethyl, propyl or butyl. In especially preferred forms, one or both of $R^{A1}$ and $R^{A4}$ are hydrogen.

When $R^{A2}$ and $R^{A3}$, together with the carbons to which they are attached, form a carbocyclic or heterocyclic group as defined above, preferably they form a 3 to 8-membered cyclic group, preferably 5 to 6-membered cyclic group. Preferably they form a cyclopentane, cyclohexane, cyclopentene, cyclohexene, cyclopentadiene, cyclohexadiene, tetrahydrofuran, dihydrofuran, pyrrolidine, pyrroline, pyran, dihydrophyran, tetrahydropyran or piperidene group. Preferably, $R^{A1}$ and $R^{A4}$ are hydrogen.

In still yet a further embodiment, Y is preferably an optionally substituted phenyl group of Formula (ii):

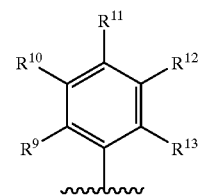

(ii)

Wherein $R^9$–$R^{13}$ are as defined for $R^1$–$R^4$ and $R^{14}$ as described above.

More preferably, $R^9$–$R^{13}$ are hydrogen; hydroxy; optionally substituted alkyl; optionally substituted alkyloxy; acyloxy; carboxy; carboxy ester, wherein the ester is preferably methyl, ethyl, propyl or butyl ester; optionally substituted amino,; carboxamido, wherein the nitrogen atom thereof is optionally substituted by one or two alkyl groups independently selected from methyl, ethyl, propyl or butyl; or sulfate. Most preferably, $R^9$–$R^{13}$ are selected from hydrogen, hydroxy, methoxy, ethoxy, iso-propoxy, methyl, ethyl, n-propyl, isopropyl, acetoxy or sulphate.

Another preferred embodiment of Formula (I) is a compound of Formula (Ia) where X is hydrogen and W is a group of the formula (iii);

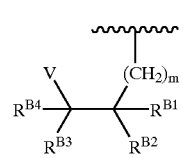

(iii)

wherein V is hydrogen or halogen; $R^{B1-B4}$ are correspondingly defined as for $R^{A1-A4}$ herein above; and m is selected from 1, 2, 3 or 4.

Thus, in a preferred embodiment, the present invention relates to a method for the preparation of a compound of Formula (IIa):

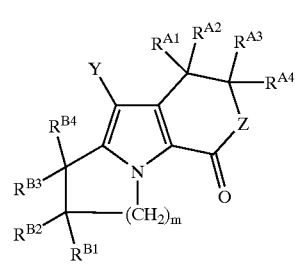

(IIa)

comprising the step of performing two intramolecular cyclizations on a compound of Formula (Ia):

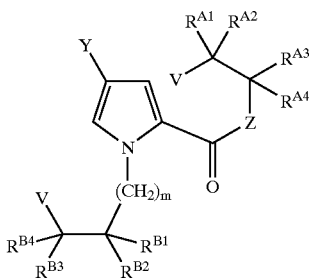

(Ia)

wherein:
$R^{A1-A4}$, V, Y, Z are as defined above;
$R^{B1-B4}$ are each independently selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano; or $R^{B2}$ and $R^{B3}$ may optionally together form a bond and $R^{A1}$ and $R^{A4}$ are as defined above or together with the carbon atoms to which they are attached form an optionally substituted carbocyclic or heterocyclic group; or $R^{B2}$ and $R^{B3}$, together with the carbon atoms to which they are attached form an optionally substituted saturated or unsaturated carbocyclic or heterocyclic group; or $R^{B1}R^{B2}C—CR^{B3}R^{B4}$ form an optionally substituted aryl group or aromatic heterocyclic group; and
m is selected from 1, 2, 3 or 4.

Another preferred embodiment of the invention provides an intermediate compound of Formula (Ia)

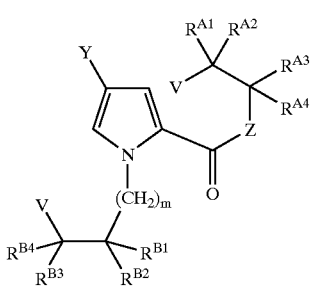

(Ia)

wherein:
$R^{A1-A4}$, $R^{B1-B4}$, V, Y, Z and m are as defined above and optionally, one or more (CH₂) groups of $(CH_2)_m$ defined in formula (iii) may be optionally substituted by a group $R^{14}$ as defined above.

In a preferred embodiment m is 1 or 2. Even more preferably in is 2.

In yet other embodiments of Compounds of Formulae (Ia) and (IIa), when $R^{B1}R^{B2}C—CR^{B3}R^{B4}$ forms an aryl group or an aromatic heterocyclic group, it may be an optionally substituted benzene or naphthalene ring or an optionally substituted aromatic heterocyclic group such as pyridine, furan, pyrrole or thiophene and benzene-fused analogues thereof, for example, quinoline, indole, benzofuran and benzothiophene. Attachment of the bicyclic heterocyclic group may be via the benzene or heterocyclic ring. Preferably $R^{B1}R^{B2}C—CR^{B3}R^{B4}$ forms an optionally substituted benzene group. Where $R^{B1}R^{B2}C—CR^{B3}R^{B4}$ forms a benzene group (containing the substituent V) cyclization can afford a group of formula (i) as described herein above. Preferably the substituents are hydrogen; hydroxy; optionally substituted alkyl; optionally substituted alkyloxy; acyloxy; carboxy; carboxy ester. wherein the ester is preferably methyl, ethyl, propyl or butyl ester; optionally substituted amino,; carboxamido, wherein the nitrogen atom thereof is optionally substituted by one or two alkyl groups independently selected from methyl, ethyl, propyl or butyl; or sulfate. Most preferably they are hydrogen, hydroxy, methoxy, ethoxy, iso-propoxy, methyl, ethyl, propyl, acetoxy or sulfate.

In another embodiment $R^{B1-B4}$ are preferably independently selected from hydrogen, optionally substituted alkyl, optionally protected hydroxy, optionally substituted alkoxy, optionally substituted phenyl or acyloxy. In one preferred embodiment, at least one of $R^{B1}$ or $R^{B3}$ may be hydrogen. In another embodiment, both $R^{B1}$ and $R^{B3}$ are hydrogen. In yet a further embodiment, three or four of $R^{B1-B4}$ are hydrogen.

In another embodiment, when $R^{B2}$ and $R^{B3}$ together form a bond so as to form a group $R^{B1}C=CR^{B4}$, $R^{B1}$ and $R^{B4}$ each may be independently selected from hydrogen; hydroxy; optionally substituted alkyl; optionally substituted alkyloxy; acyloxy; carboxy; carboxy ester, wherein the ester is preferably methyl, ethyl, propyl or butyl ester; optionally substituted amin or; carboxamido, wherein the nitrogen atom thereof is optionally substituted by one or two alkyl groups independently selected from methyl, ethyl, propyl or butyl. In especially preferred forms, one or both of $R^{A1}$ and $R^{A4}$ are hydrogen.

When $R^{B2}$ and $R^{B3}$, together with the carbons to which they are attached, form a carbocyclic or heterocyclic group as defined above, preferably they form a 3 to 8-membered cyclic group, preferably 5 to 6-membered cyclic group. Preferably they form a cyclopentane, cyclohexane, cyclopentene, cyclohexene, cyclopentadiene, cyclohexadiene, tetrahydrofuran, dihydrofuran, pyrrolidine, pyrroline, pyran, dihydrophyran, tetrahydropyran or piperidene group. Preferably, $R^{B1}$ and $R^{B4}$ are hydrogen.

Especially preferred compounds of Formula (I) have the structure of Formula (Ib) below:

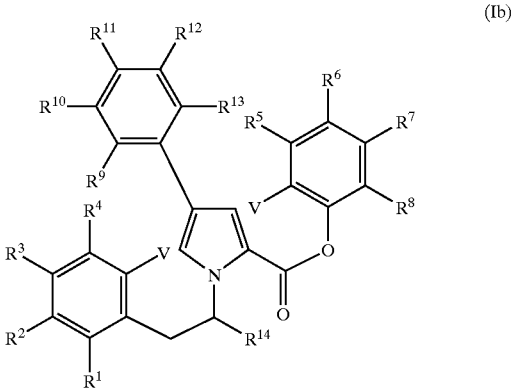

(Ib)

where $R^1–R^{14}$ are independently selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyan. Preferred $R^1$–$R^{14}$ are selected from hydrogen; hydroxy; optionally substituted alkyl; optionally substituted alkyloxy; acyloxy; carboxy; carboxy ester, wherein the ester is preferably methyl, ethyl, propyl or butyl ester; optionally substituted amino, such as mono or dialkyl amino; carboxamido, wherein the nitrogen atom thereof is optionally substituted by one or two alkyl groups independently selected from methyl, ethyl, propyl or butyl; or sulfate.

More preferably $R^1$–$R^{13}$ are selected from hydrogen; hydroxy; optionally substituted alkyl, such as methyl, ethyl or propyl; optionally substituted alkyloxy such as methoxy, ethoxy, n-propoxy, iso-propoxy; acyloxy such as acetoxy; or sulfate and R14 is preferably hydrogen or hydroxy. V is as defined above, preferably hydrogen, iodine or bromine.

Thus a further preferred form of the invention provides a method of preparing a fused polycyclic pyrrole-containing compound of Formula (IIb):

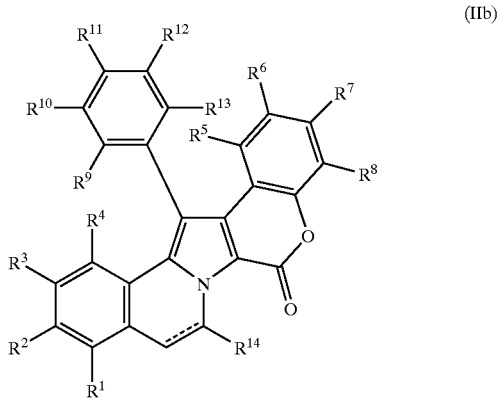

(IIb)

comprising the step of performing two cyclizations on a compound of Formula (Ib).

The intramolecular cyclizations of compounds of Formula (I), preferably of Formula (Ia) or (Ib), to form the polycyclic fused compounds of Formula (II), preferably of Formula (Ia) or (IIb) can be carried out by any suitable means known to those skilled in the art. Suitable methods are described below, however, any other method which will effect the desired cyclization also forms part of the present invention. It will be understood that the groups V, W, X, Y, Z, $R^{A1-A4}$, $R^{B1-B4}$, and $R^{1-14}$ are such that they do not interfere with the cyclization process.

Where V represents a hydrogen atom, an oxidative intramolecular cyclization process, such as those described by Black et al, *Tetrahedron Lett.*, 1989, 30, 5807 and Kita et al, *Chem. Commum*, 1996, 1481, may be used to effect the cyclization.

Alternatively, when V is a halogen atom, the intramolecular cyclization may proceed via the generation of a suitable radical in an analogous manner to those described by Antonio et al, *Can. J. Chem.*, 1994, 72, 15 and Moody et al, *Tetrahedron Lett.*, 1995, 36, 9501.

Yet another method for intramolecularly cyclizing a compound of Formula (I), when V is halogen, involves a Pd[0]-mediated cyclization. The intramolecular Pd[0]-catalyzed olefination of an organic halide (intramolecular Heck Reaction) is known to those skilled in the art and can be carried out by any suitable combination of reagents which will provide palladium in the zero state (Pd[0]).

Suitable combinations of reagents for effecting Pd[0]-catalysed cyclization are described, for example, in Burwood et al, *Tetrahedron Lett.*, 1995, 36, 9053; Desarbe et al, *Heterocycles*, 1995, 41, 1987; Harayoma et al, *Chem. Pharm. Bull.*, 1997, 45, 1723; and Grigg et al, *Tetrahedron*, 1995, 50, 359.

Thus, in one embodiment of the invention, Pd[0]-catalysed cyclization of Formula (I) may be effected by generating Pd[0] in situ by a combination of a Pd[II] reagent and a "ligand", and further providing a base for regeneration of the Pd[0] catalyst.

Suitable examples of a Pd[II]/Pd[0] reagent include, but are not limited to: $Pd(OAc)_2$, $PdCl_2(CH_3CN)_2$, $PdCl_2(PPh_3)_2$, $Pd(C_6H_5CN)_2Cl_2$, $Pd(dibenzylideneacetone)_3$.

Suitable examples of "ligand" providing reagents include, but are not limited to: $PPh_3$, $P(o\text{-tolyl})_3$; 1,3-bis[diphenylphosphino]propane and 1, 3-bis[diphenylphosphino]ethane.

Suitable bases for regenerating Pd[0] from Pd[II], which is formed during the Pd[0]-catalysed cyclization, include, but are not limited to; alkylamines, such as triethylamine and diisopropylethylamine; acetates, such as sodium acetate and potassium acetate; carbonates such as potassium carbonate, sodium carbonate, silver carbonate; and hydroxides such as sodium and potassium hydroxide.

When a compound of Formula (Ia) or (Ib) is treated to effect a double cyclization, to form compounds of Formula (Ia) or (IIb), the cyclizations may be effected by the radical, oxidative or Pd-mediated cyclization procedures as described above, and each cyclization may be effected in the same, similar or different manner.

Thus, in one embodiment, the two cyclizations may be performed sequentially, in any order, and may optionally employ different reagents and conditions, for example as described above. Optionally, after one cyclization, is performed, the mono-cyclized product may be isolated before being treated under suitable sonditions to perform the second intramolecular cyclization. In another form, the "double cyclization" may be effected in "one-pot", preferably under a single set of reaction conditions.

In a more preferred form, a compound of Formula (Ia), preferably (Ib), is made to undergo a "double cyclization" to form a compound of Formula (IIa), preferably (IIb), under Pd[0]-catalysed conditions.

In an even more preferred form, both cyclizations are effected in "one-pot" under a single set of reaction conditions.

The compounds of Formula (I), (Ia) and (Ib) may be prepared, starting from a pyrrole core, by standard procedures known to the skilled addressee for effecting substitution of the carbon atoms of the pyrrole core, for example by electrophilic aromatic substitution or halogenating the pyrrole nucleus and effecting a substitution by Stille, Suzuki, or Negishi cross-coupling reactions with stannane, boronic acid or zinc compounds such as aryl-stannanes, aryl boronic acid and aryl zinc compounds. Substitution of the N-atom can be effected by standard procedures.

One suitable approach, although by no means limiting, is depicted below in Scheme 1 which is considered to be illustrative of suitable methods for substituting the pyrrole nucleus.

It will be understood that by use of the appropriate reagents in steps used to introduce the 1-, 2-, 4-substitution pattern of the pyrrole core, for example, the phenyl containing reagents used in steps, (d), (e) and (f) wherein the phenyl moiety is further substituted as hereinbefore described, a range of substitution patterns and substituents may be introduced to form the intermediates amenable to the cyclization processes and the formation of the corresponding cyclized compounds.

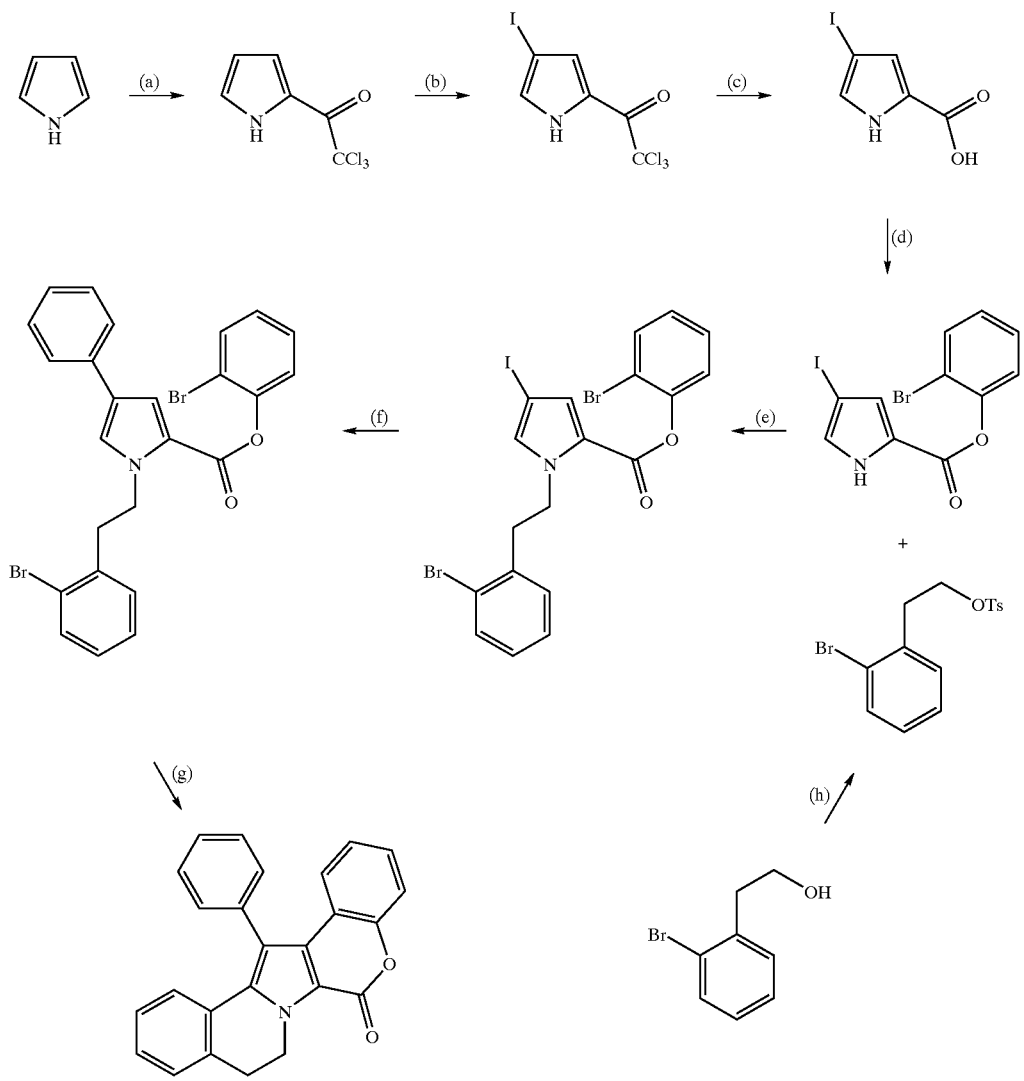

Scheme 1

Reagents and conditions: (a) Cl$_3$CCOCl (1 mole equiv.), Et$_2$O, 35° C., 1 h (80%); (b) I$_2$ (1 mole equiv.), AgO$_2$CCF$_3$ (1 mole equiv.), CHCl$_3$, 18° C., 1 h (82%); (c) K$_2$CO$_3$ (2M in H$_2$O), DMSO, 18° C., 32 h (92%); (d) (i) (COCl)$_2$ (1.1 mole equiv.), DMF (cat.), CH$_2$C$_2$, 18°° C., 2 h; (ii) o-bromophenol (1 mole equiv.), DMAP (cat.), CH$_2$Cl$_2$, 18° C., 1 h (92%); (e) K$_2$CO$_3$ (1.14 mole equiv.), Bu$_4$NCl (0.1 mole equiv.), DMF, 80° C., 2 h (90%): (f) PhZnCl (1.3 mole equiv.), PdCl$_2$(PPh$_3$)$_2$ (0.05 mole equiv.), THF/DMF, 18° C., 1 h (95%); (g) Pd(OAc)$_2$ (0.5 mole equiv.), PPh$_3$ (1 equiv.), NaOAc (4 equiv.), DMF, 130° C., 6 h (16%); (h) TsCl (2.4 mole equiv.), KOH (2.4 mole equiv.), Et$_2$O, 0®18° C., 2 h (98%).

Where the optional double bond is present, as in the compounds of Formula (II) which contain moiety of Formula (I), such as compounds of Formula (IIb), this may be introduced either by dehydrogenation of the cyclized product, or alternatively, by incorporation of the corresponding double bond into a precursor thereof. Suitable methods therefor will be known to the skilled addressee (see for example, *Advanced Organic Chemistry, Reactions, Mechanisms, and Structure* by Jerry March, Third Edition, Wiley Interscience). One such suitable method comprises treating the cyclized compound of Formula (IIb), with DDQ (2,3-Dichloro-5,6-dicyano-1,4-benzoqionone). For example, Lamellarin T diisopropylether (Compound 37 in Table 2) can be converted into Lamellarin W diisopropylether (Compound 11 in Table 1) by treatment with DDQ in dry chloroform at 60–65 C. (see Example 11 in WO98/50365)

WO 97/01336 (the entire contents of which are taken to be incorporated herein by reference) describes Lamellarin class compounds as having inhibitory and/or cytotoxic activity against multidrug resistant-type tumours.

Accordingly, yet another aspect of the present invention contemplates a method of treatment comprising the administration of a treatment effective amount of a compound of general Formula (II), as prepared by the methods described herein, as an active ingredient, to an animal, including a human, in need thereof.

As used herein, the term "effective amount" relates to an amount of compound which, when administered according to a desired dosing regimen, provides the desired therapeutic activity. The dose will depend on the age, weight and condition of the subject and it is within the skill of the attending physician to determine suitable doasages. Dosing may occur at intervals of minutes, hours, days, weeks, months or years or continuously over any one of these periods. Suitable dosages lie within the range of about 0.1 ng per kg of body weight to 1 g per kg of body weight per dosage. Preferably, the dosage is in the range of 1 μg to 1 g per kg of body weight per dosage. More preferably, the dosage is in the range of 1 mg to 1 g per dosage per kg of body weight. Suitably, dosages are in the range of about 1 mg to 500 mg per kg of body weight, such as between 1 mg and 250 mg or 1 mg and 100 mg.

In a preferred embodiment, the method of treatment relates to treating multidrug resistant tumors.

In another embodiment, the method of treatment contemplates improving the antitumor chemotherapeutic effect of multidrug resistant affected drugs.

In another preferred embodiment, the method of treatment is a method for inducing apoptosis. More preferably, the method of treatment is a method of inducing apoptosis on a multidrug resistant cell.

In another embodiment, the method of treatment contemplates modulating immunological functions.

The active ingredient may be administered in a single dose or a series of doses. While it is possible for the active ingredient to be administered alone, it is preferable to present it as a composition, preferably as a pharmaceutical composition.

Yet another aspect of the invention contemplates compositions comprising a compound of general Formula (II), as prepared according to the present invention, together with a pharmaceutically acceptable carrier, excipient or diluent.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions for rectal administration may be presented as a suppository with a suitable base comprising, for example, cocoa butter.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The present invention also provides the use of a compound of general Formula (II), as prepared according to the present invention, in the manufacture of a medicament for treatment of an animal or human in need thereof.

Another aspect of the invention contemplates an agent for the treatment of an animal or human in need thereof comprising a compound of general Formula (II), as prepared according to the present invention.

In a first embodiment, the agent is for treating multidrug resistant tumors.

In another embodiment the agent is for inducing apoptosis on a multi-drug resistant cell.

In yet another embodiment, the agent is for improving the anti-tumor chemotherapeutic effect of multidrug resistant affected drugs.

A further embodiment is an agent for modulating immunological functions.

Suitable, although by no means limited, examples of compounds which may be prepared via the intermediates of the present invention are depicted below in Tables 1 and 2:

TABLE 1

| Compound | $R^1$ | $R^2$ | $R^3$ | $R^4$ $R^5$ | $R^6$ | $R^7$ | $R^8$ $R^9$ | $R^{10}$ | $R^{11}$ | $R^{12}$ $R^{13}$ |
|---|---|---|---|---|---|---|---|---|---|---|
| 1 | H | H | H | H | H | H | H | H | H | H |
| 2 (Lamellarin B) | OMe | OMe | OMe | H | OMe | OH | H | OMe | OH | H |
| 3 (Lamellarin D) | H | OH | OMe | H | OMe | OH | H | OMe | OH | H |
| 4 (Lamellarin D-triacetate) | H | OAc | OMe | H | OMe | OAc | H | OMe | OAc | H |
| 5 (Lamellarin M) | OH | OMe | OMe | H | OMe | OH | H | OMe | OH | H |
| 6 (Lamellarin M-triacetate) | OAc | OMe | OMe | H | OMe | OAc | H | OMe | OAc | H |
| 7 (Lamellarin N) | H | OH | OMe | H | OMe | OH | H | OH | OMe | H |
| 8 (Lamellarin N-triacetate) | H | OAc | OMe | H | OMe | OAc | H | OAc | OMe | H |
| 9 (Lamellarin W) | OMe | OMe | OMe | H | OMe | OH | H | OH | OMe | H |
| 10 (Lamellarin X) | OH | OMe | OMe | H | OMe | OH | H | OH | OMe | H |
| 11 | OMe | OMe | OMe | H | OMe | O$^i$Pr | H | O$^i$Pr | OMe | H |

TABLE 2

| Compound | $R^1$ | $R^2$ | $R^3$ | $R^4$ $R^5$ | $R^6$ | $R^7$ | $R^8$ $R^9$ | $R^{10}$ | $R^{11}$ | $R^{12}$ $R^{13}$ | $R^{14}$ |
|---|---|---|---|---|---|---|---|---|---|---|---|
| 12 (Lamellarin A) | OMe | OMe | OMe | H | OMe | OH | H | OMe | OH | H | OH |
| 13 (Lamellarin C) | OMe | OMe | OMe | H | OMe | OH | H | OMe | OH | H | H |
| 14 (Lamellarin E) | OH | OMe | OMe | H | OMe | OH | H | OH | OMe | H | H |

TABLE 2-continued

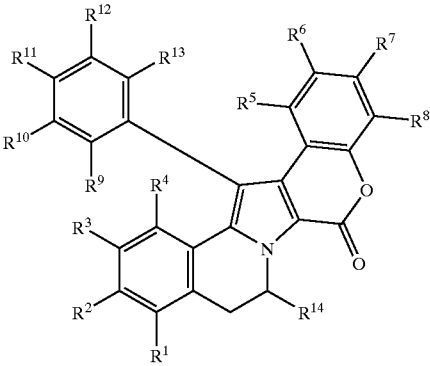

| Compound | R¹ | R² | R³ | R⁴ R⁵ | R⁶ | R⁷ | R⁸ R⁹ | R¹⁰ | R¹² R¹¹ | R¹³ | R¹⁴ |
|---|---|---|---|---|---|---|---|---|---|---|---|
| 15 (Lamellarin F) | OH | OMe | OMe | H | OMe | OH | H | OMe | OMe | H | H |
| 16 (Lamellarin G) | H | OH | OMe | H | OH | OMe | H | OH | OMe | H | H |
| 17 (Lamellarin H) | H | OH | OH | H | OH | OH | H | OH | OH | H | H |
| 18 (Lamellarin I) | OMe | OMe | OMe | H | OMe | OH | H | OMe | OMe | H | H |
| 19 (Lamellarin I-acetate) | OMe | OMe | OMe | H | OMe | OAc | H | OMe | OMe | H | H |
| 20 (Lamellarin J) | H | OH | OMe | H | OMe | OH | H | OMe | OMe | H | H |
| 21 (Lamellarin K) | OH | OMe | OMe | H | OMe | OH | H | OMe | OH | H | H |
| 22 (Lamellarin K-triacetate) | OAc | OMe | OMe | H | OMe | OAc | H | OMe | OAc | H | H |
| 23 (Lamellarin L) | H | OH | OMe | H | OMe | OH | H | OH | OMe | H | H |
| 24 (Lamellarin L-triacetate) | H | OAc | OMe | H | OMe | OAc | H | OAc | OMe | H | H |
| 25 (Lamellarin S) | H | OH | OMe | H | OH | OH | H | OH | OH | H | H |
| 26 (Lamellarin T) | OMe | OMe | OMe | H | OMe | OH | H | OH | OMe | H | H |
| 27 (Lamellarin T20-sulfate) | OMe | OMe | OMe | H | OMe | OSO₃Na | H | OMe | OH | H | H |
| 28 | H | OMe | OMe | H | H | H | H | H | H | H | H |
| 29 (Lamellarin U) | H | OMe | OMe | H | OMe | OH | H | OH | OMe | H | H |
| 30 (Lamellarin U20-sulfate) | H | OMe | OMe | H | OMe | OSO₃Na | H | OH | OMe | H | H |
| 31 (Lamellarin V) | OMe | OMe | OMe | H | OMe | OH | H | OH | OMe | H | OH |
| 32 (Lamellarin V20-sulfate) | OMe | OMe | OMe | H | OMe | OSO₃Na | H | OH | OMe | H | OH |
| 33 (Lamellarin Y20-sulfate) | H | OMe | OH | H | OMe | OSO₃Na | H | OH | OMe | H | H |
| 34 | H | OMe | OMe | H | OMe | OⁱPr | H | OMe | OⁱPr | H | H |
| 35 | H | OMe | OMe | H | OMe | OH | H | OMe | OH | H | H |
| 36 | OⁱPr | OMe | OMe | H | OMe | OⁱPr | H | OMe | OⁱPr | H | H |
| 37 | OMe | OMe | OMe | H | OMe | OⁱPr | H | OⁱPr | OMe | H | H |
| 38 | H | OMe | OMe | H | OMe | OⁱPr | H | OⁱPr | OMe | H | H |
| 39 (Lamellarin T diacetate) | OMe | OMe | OMe | H | OMe | OAc | H | OAc | OMe | H | H |

The invention will now be described with reference to the following Examples. However, it is to be understood that these do not supercede the generality of the preceding description.

EXAMPLES

Example 1

2-(Trichloroacetyl)pyrrole 2-(Trichloroacetyl)pyrrole was prepared from pyrrole (12.5 g, 186 mmol) and trichloroacetyl chloride (36.5 g, 200 mmol) according to the method of Bailey et al, *Org. Synth.*, 1971, 100. In this manner the title compound (31.3 g, 80%) was obtained as a cream solid, m.p. 73–74° C. (lit. m.p. 73–75° C.). ¹H n.m.r. d 9.30, broad s, 1H; 7.39, m, 1H; 7.17, m, 1H; 6.40, dt, J 3.9 and 2.4 Hz, 1H. (see also *J. Org. Chem.*, 1972, 37, 3618; 1993, 58, 7245).

4-Iodo-2-(trichloroacetyl)pyrrole

The title compound was prepared from 2-(trichloroacetyl) pyrrole according to the method of Bélanger, *Tetrahedron Lett.*, 1979, 2505. Thus, iodine (12.0 g, 47.2 mmol) was added portionwise (approximately 1 g per portion) over 0.17 h to a magnetically stirred mixture of silver trifluoroacetate (11.0 g, 49.8 mmol) and 2-(trichloroacetyl)pyrrole (10.0 g, 47.1 mmol) in dry chloroform (70 ml) maintained at 0° C. (ice-bath). After addition was complete the reaction mixture was allowed to warm to 18° C. and stirred at this temperature for a further 2 h. The resultant suspension was filtered through a sintered glass funnel (No. 3 porosity) and the filtrate washed with Na₂S₂O₅ (1×80 ml of 5% w/v aqueous solution) and water (2×80 ml) then dried (MgSO₄), filtered and concentrated under reduced pressure. The solid residue thus obtained was treated with hexane/ether (50 ml of a 4:1 v/v mixture) and the resulting suspension stirred at 18° C. for 5 h then the solid was filtered off to give the title compound (13.1 g, 82%) as a cream solid, m.p. 129–130° C. (lit. m.p. 128–130° C.). $^1$H n.m.r. d 9.45, broad s, 1H; 7.44, dd, J 2.6 and 1.3 Hz, 1H; 7.19, dd, J 2.6 and 1.3 Hz, 1H.

4-Iodopyrrole-2-carboxylic acid $K_2CO_3$ (100 ml of a 2 M aqueous solution) was added to a solution of 4-iodo-2-(trichloroacetyl)pyrrole (8.5 g, 2.5 mmol) in dmso (30 ml) and the resulting mixture stirred at 18° C. for 3 h then diluted with $H_2O$ (200 ml). The solution thus obtained. was washed with ethyl acetate (2×100 ml) then acidified, by dropwise addition of HCl (2 M aqueous solution), to pH 3. The resulting slurry was extracted with ethyl acetate (3×100 ml) and the combined organic fractions were dried ($MgSO_4$), filtered and concentrated under reduced pressure to give the title compound (8) (5.51 g, 92%) as a white solid, m.p. 200° C. (Found: $M^{+\cdot}$, 236.9285. $C_5H_4INO_2$ requires $M^{+\cdot}$, 236.9287). $n_{max}$ (KBr) 3287, 3129, 3035, 1703, 1544, 1430, 1300, 1212, 1122 $cm^{-1}$. $^1$H n.m.r. [300 MHz, 3:1 $(CD_3)_2SO/CDCl_3$] d 11.98, broad s, 1H; 6.98, t, J 1.5 Hz, 1H; 6.76, broadened s, 1H (resonance due to N—H not observed). $^{13}$C n.m.r. [75.5 MHz, 3:1 $CD_3)_2SO/CDCl$] d 159.0 (C), 126.0 (CH), 123.3 (C), 118.8 (CH), 59.0 (C). Mass spectrum m/z 237 (100%) ($M^{+\cdot}$); 219 (87) [$(M-H_2O)^{+\cdot}$].

2-Bromophenyl 4-Iodopyrrole-2-carboxylate

Oxalyl chloride (203 mL, 2.32 mmol) was added to a magnetically stirred suspension of 4-iodopyrrole-2-carboxylic acid (8) (500 mg, 2.11 mmol) in dry $CH_2Cl_2$ (15.0 ml) containing dmf (1 drop). After stirring the resulting solution at 18° C. for 2 h it was added to a magnetically stirred solution of o-bromophenol (363 mg, 2.11 mmol), triethylamine (660 ml, 4.73 mmol) and 4-(N,N-dimethylamino)pyridine (dmap, several crystals) in $CH_2Cl_2$ (10 ml). After 1 h the reaction mixture was concentrated onto silica gel (5 g) and the residue subjected to flash chromatography (silica gel, 3:1 hexane/ether elution). Concentration of the appropriate fractions ($R_f$ 0.2) then gave the title compound (761 mg, 92%) as a white crystalline solid, m.p. 126–127° C. (Found: C, 33.9; H, 1.7; Br, 20.4; I, 32.4; N, 4.0. $C_{11}H_7BrINO_2$ requires C, 33.7; H, 1.8; Br, 20.4; I, 32.4; N, 3.6%). $n_{max}$ (KBr) 3383, 2969, 1709, 1580, 1541, 1472, 1444, 1377, 1312, 1218, 1169, 1133, 1043 $cm^{-1}$. $^1$H n.m.r. d 9.57, broad s, 1H; 7.65, dd, J 8.1 and 1.5 Hz, 1H; 7.37, td, J 8.1 and 1.5 Hz, 1H; 7.27, m, 2H; 7.18, td, J 8.1 and 1.5 Hz, 1H; 7.08, m, 1H. $^{13}$C n.m.r. d 158.0 (C), 148.3 (C), 134.0 (CH), 129.8 (CH), 129.1 (CH), 128.1 (CH), 124.4 (CH), 124.3 (CH), 123.6 (C), 116.9 (C), 62.9 (C). Mass spectrum m/z 393 (24%) 391 (22) ($M^{+\cdot}$); 220 (100) [$(M-C_6H_4BrO)^{+\cdot}$].

2-(2-Bromophenyl)ethyl 4-Methylbenzenesulfonate (13)

A magnetically stirred solution of 2-bromophenethyl alcohol (5.00 g, 24.9 mmol, ex ALDRICH) and 4-methylbenzenesulfonyl chloride (11.20 g, 59.7 mmol) in diethyl ether (50 ml) was cooled to 0° C. (ice-bath) then treated with powdered KOH (3.2 g, 2.4 mole equiv.). The reaction mixture thus obtained was allowed to warm to 18° C., stirred at this temperature for 2.0 h then diluted with water (100 ml). The separated organic phase was washed with water (1×100 ml) then dried ($MgSO_4$), filtered and concentrated under reduced pressure to give a white solid. Since this material contained residual 4-methylbenzenesulfonyl chloride it was dissolved in pyridine (75 ml) and the resulting solution stirred at 18° C. for 0.16 h then diluted with water (500 ml) and extracted with diethyl ether (1×500 ml). The separated organic phase was washed with HCl (1×250 ml of a 5 M aqueous solution) then sodium hydrogen carbonate (1×250 ml of a 0.5 M aqueous solution) before being dried ($MgSO_4$), filtered and concentrated under reduced pressure to give the title compound (8.66 g, 98%) as white crystalline masses, m.p. 39–39.5° C. (Found: C, 50.9; H, 4.2; Br, 22.6; S, 8.8. $C_{15}H_{15}BrO_3S$ requires C, 50.7; H, 4.3; Br, 22.5; S, 9.0%). $n_{max}$ (KBr) 1356, 1177, 1021, 980, 962, 895, 812, 769, 752, 665, 557 $cm^{-1}$. $^1$H n.m.r. d 7.68, d, J 8.3 Hz, 2H; 7.45, d, J 7.7 Hz, 1H; 7.27, d, J 8.3 Hz, 2H; 7.17, m, 2H; 7.07, m, 1H; 4.25, t, J 7.0 Hz, 2H; 3.09, t, J 7.0 Hz, 2H; 2.43, s, 3H. $^{13}$C n.m.r. d 144.5 (C), 135.3 (C), 132.7 (CH), 132.8 (C), 131.3 (CH), 129.7 (CH), 128.5 (CH), 127.6 (CH), 127.4 (CH), 124.2 (C), 68.6 ($CH_2$), 35.5 ($CH_2$), 21.5 ($CH_3$). Mass spectrum m/z 356 (0.7%) 354 (0.7) ($M^{+\cdot}$); 184 (98) 182 (100) [$M—H_3CC_6H_4SO_3H)^{+\cdot}$]; 171 (49) 169 (51); 155 (45); 103 (32); 91 (80) ($C_7H_7$+).

2-Bromophenyl 1-[2'-(2"-Bromophenyl)ethyl]-4-iodopyrrole-2-carboxylate

Compound (13) (700 mg, 1.97 mmol), tetraethyl ammonium chloride (30 mg, 0.18 mmol) and $K_2CO_3$ (278 mg, 2.0 mmol) were added to a solution of compound (11) (700 mg, 1.79 mmol) in dry dmf (30 ml) and the resultant slurry stirred at 80° C. for 2 h. The cooled reaction mixture was diluted with ethyl acetate (150 ml) and washed with water (3×150 ml). The separated organic phase was then dried ($MgSO_4$), filtered and concentrated under reduced pressure. The solid residue thus obtained was subjected to flash chromatography (silica gel, 4:1 hexane/ether elution) and concentration of the appropriate fractions ($R_f$ 0.5, 3:1 hexane/ether elution) gave the title compound (14) (920 mg, 89%) as a white crystalline solid, m.p. 122–123° C. (Found: C, 39.5; H, 2.1; Br, 27.6; I, 22.1; N, 2.3. $C_{19}H_{14}Br_2INO_2$ requires 2.5; Br, 27.8; I, 22.1; N, 2.4%). $n_{max}$ (KBr) 2949, 1716, 1517, 1468, 1438, 1411, 1374, 1326, 1232, 1216, 1191, 1055, 1028 $cm^{-1}$. $^1$H n.m.r. d 7.65, dd, J 7.8 and 1.8 Hz, 1H; 7.55, dd, J 7.8 and 1.8 Hz, 1H; 7.37, m, 2H; 7.28–7.04, m, 5H; 6.70, d, J 2.1 Hz, 1H; 7.55, dd, J 2H; 3.20, t, J 7.5 Hz, 2H. $^{13}$C n.m.r. d 157.0 (C), 147.8 (C), 136.9 (C), 134.5 (CH), 133.3 (CH), 132.7 (CH), 131.2 (CH), 128.6 (CH), 128.4 (CH), 127.6 (CH), 127.3 (CH), 126.7 (CH), 124.4 (C), 124.0 (CH), 122.0 (C), 116.6 (C), 59.6 (C), 49.0 ($CH_2$), 38.0 ($CH_2$). Mass spectrum m/z 577 (1%) 575 (2) 573 (1) ($M^{+\cdot}$); 496 (10) 494 (11) [$(M-BrO^\cdot)^+$]; 404 (98) 402 (100) [$M—C_6H_4BrO^\cdot)^+$].

2-Bromophenyl 1-[2'-(2"-Bromophenyl)ethyl]4-phenylpyrrole-2-carboxylate (4)

Phenylzinc chloride [prepared by the addition of anhydrous zinc chloride. (540 mg, 3.96 mmol) to a solution of phenyllithium (2.0 ml of a 1.8 M solution in cyclohexane/ether, 3.6 mmol) in thf (4.0 ml)] was added dropwise, over 2 min., to a magnetically stirred solution of compound (14) (1.75 g, 3.04 mmol) and $Pd(PPh_3)_2Cl_2$ (106 mg, 0.152 mmol) in dmf (15 ml). Stirring was continued at 18° C. for 1 h then the reaction mixture was transferred to a separatory funnel, diluted with ethyl acetate (100 ml) and washed with $NH_4Cl$ (100 ml of a saturated aqueous solution) then $H_2O$ (2×100 ml). The separated organic phase was dried ($MgS_4O$), filtered and concentrated under reduced pressure to give light-yellow oil which was subjected to flash chromatography (silica, 2:1 hexane/$CH_2Cl_2$ elution). Concentration of the appropriate fractions ($R_f$ 0.5) gave the title compound (1.52 g, 95%) as a microcrystalline solid, m.p.

90–92° C. (Found: C, 57.1; H, 3.4; Br, 30.7; N, 2.5. $C_{25}H_{19}Br_2NO_2$ requires C, 57.2; H, 3.7; Br, 30.4; N, 2.7%). $m_{max}$ (KBr) 2958, 2930, 1718, 1603, 1580, 1562, 1472, 1397, 1215, 1196, 1066, 1024 cm$^{31}$ . $^1$H n.m.r. d 7.70, dd, J 8.0 and 1.5 Hz, 1H; 7.60–7.00, m, 14H; 4.63, t, J 6.9 Hz, 2H; 3.32, t, J 6.9 Hz, 2H. $^{13}$C n.m.r. (75.5 MHz, CDCl$_3$) d 158.4 (C), 148.3 (C), 137.5 (C), 134.2 (C), 133.5 (CH), 132.9 (C), 131.5 (CH), 128.9 (CH), 128.6(3) (CH), 128.6(1) (CH), 127.8 (CH), 127.4 (CH), 127.3 (CH), 126.5 (CH), 125.4 (CH), 124.8 (C), 124.6 (C), 124.4 (CH), 120.9 (C), 117.5 (CH), 116.9 (C), 49.3 (CH$_2$), 38.2 (CH$_2$). Mass spectrum m/z 527 (3%) 525 (6) 523 (3) (M$^{+\cdot}$); 446 (12) 444 (11) [(M–Br)$^+$]; 354 (100) 352 (96) [M–C$_6$H$_4$BrO$^\cdot$)$^+$].

14-Phenyl-8,9-dihydro-6H-[1]benzopyrano[4',3':4,5]pyrrolo[2,1-a]isoqinolin-6one

Pd(OAc)$_2$ (32 mg, 0.143 mmol) was added to a magnetically stirred solution of compound (4) (148 mg, 0.282 mmol), NaOAc (92.7 mg, 1.13 mmol) and PPh$_3$ (74.0 mg, 0.282 mmol) in dmf (2 ml) contained in a Schlenk tube. The resulting mixture was evacuated (1.0 mmHg) and back-filled with N$_2$ (gas) three times (to remove dissolved oxygen) then heated under nitrogen at 135° C. for 6 h. The cooled reaction mixture was diluted with ether (25 mL) and washed with brine (2×20 ml) then water (20 ml) before being dried (MgSO$_4$), filtered and concentrated onto silica (2 g). The residue was subjected to flash chromatography (silica, 1:2, 1:1 then 2:1 CH$_2$Cl$_2$/hexane elution) and the appropriate fractions (R$_f$ 0.3, 2:1 CH$_2$Cl$_2$/hexane elution) were concentrated under reduced pressure to give the title compound (16 mg, 16%) as a cream-coloured microcrystals, m.p. 259–260° C. (Found: M$^{+\cdot}$, 363.1257. C$_{25}$H$_{17}$NO$_2$ requires M$^{+\cdot}$, 363.1259). n$_{max}$ (KBr) 2925, 2853, 1708, 1449, 1420, 1396, 1339, 1281, 1241, 1198, 1151, 1133, 1106, 1085, 1047 cm$^{-1}$. $^1$H n.m.r. d 7.58–7.55, m, 2H; 7.51–7.50, m, 2H; 7.40, dd, J 7.5 and 0.9 Hz, 1H; 7.32–7.18, m, 4H; 7.10, dd, J 7.8 and 1.2 Hz, 1H; 7.01–6.97, m, 3H; 4.88, t, J 6.9 Hz, 2H; 3.21, t, J 6.9 Hz, 2H. 13C n.m.r. d 155.3 (C), 151.2 (C), 135.6 (C), 135.3 (C), 133.8 (C), 130.7 (CH), 129.4 (CH), 128.3 (CH), 128.1 (CH), 127.5 (C), 127.4 (CH), 126.9 (CH), 125.7 (CH), 123.7 (CH), 123.3 (CH), 118.2 (CH), 117.5 (C), 117.1 (CH), 42.3 (CH$_2$), 29.3 (CH$_2$) (three peaks obscured or overlapping). Mass spectrum m/z 363 (100%) (M$^+$).

2'-Bromophenyl 5,6-Dihydro-1-phenylpyrrolo[2,1-a]isoquinoline-3-carboxylate (16) and Bromo{2'-(5",6"-dihydro-1"-phenylpyrrolo[2",1"-a]isoquinoline-3"-carboxy)phenyl}bis(triphenylphosphine)palladium (17)

Pd(OAc)$_2$ (197 mg, 0.88 mmol) was added to a solution of compound (4) (230 mg, 0.438 mmol), NaOAc (80 mg, 0.975 mmol) and PPh$_3$ (460 mg, 1.75 mmol) in dmf (20 ml). The solution was evacuated (1.0 mmHg) and back-filled with N$_2$ (gas) three times to remove dissolved oxygen and then heated under nitrogen at 110° C. for 19 h. The cooled reaction mixture was diluted with ethyl acetate (25 ml) then washed with brine (2×20 ml) and water (1×20 ml). The separated organic phase was then dried (MgSO$_4$), filtered and concentrated under reduced pressure onto silica (2 g). Subjection of the resulting material to flash chromatography (silica, 1:2 then 1:1 CH$_2$Cl$_2$/hexane followed by 4:1 CH$_2$Cl$_2$/ethyl acetate elution) gave two fractions, A and B.

Concentration of fraction A (R$_f$ 0.6, 2:1 CH$_2$Cl$_2$/hexane elution) afforded compound (16) (34 mg, 17%) as off-white crystalline masses, m.p. 130–131° C. (Found: M$^{+\cdot}$, 443.0529. C$_{25}$H$_{18}$$^{79}$BrNO$_2$ requires M$^{+\cdot}$, 443.0521). n$_{max}$ (KBr) 2950, 1710, 1471, 1439, 1418, 1240, 1212, 1176, 1046 cm$^{-1}$. $^1$H n.m.r. d 7.57, dd, J 8.1 and 1.5 Hz, 1H; 7.45–7.05, m, 12H; 6.95, br t, J 8.1 Hz, 1H; 4.57, t, J 6.3 Hz, 2H; 3.05, t, J 6.3 Hz, 2H. $^{13}$C n.m.r. d 158.5 (C), 148.1 (C), 136.1 (C), 133.4 (C), 133.3 (CH), 132.9 (C), 129.1 (CH), 128.6 (C), 128.4 (CH), 128.1 (C), 127.9 (CH), 127.7 (CH), 127.1 (CH), 126.9(CH), 126.7 (CH), 125.5 (CH), 124.2 (CH), 123.5 (C), 121.3 (CH), 119.4 (C), 116.7 (C), 42.4 (CH$_2$), 29.5 (CH$_2$). Mass spectrum m/z 445 (10%) 443 (9) (M$^{+\cdot}$); 272 (100) [(M–C$_6$H$_4$BrO$^\cdot$)$^+$].

Concentration of fraction B (R$_f$ 0.1, CH$_2$Cl$_2$elution) afforded compound (17) (40 mg, 8.5%) as off-white crystalline masses, m. p. 159–162° C. n$_{max}$ (KBr) 3052, 2923, 1705, 1481, 1435, 1416, 1238, 1172, 1095, 1058, 1024 cm$^{-1}$. $^1$H n.m.r. d 7.65–7.40, m, 18H; 7.30–7.05, m, 22H; 6.58, m, 1H; 6.52, t, J 6.6 Hz, 1H; 6.39, m, 1H; 6.07, q, J 6.6 Hz, 1H; 4.73, m, 2H; 3.05, m, 2H. $^{13}$C n.m.r. d 159.2 (C), 151.8 (C), 138.3 (CH), 136.5 (C), 134.8 (CH), 133.2 (C), 131.8 (C), 131.5 (C), 131.0 (C), 129.9 (CH), 129.8 (CH), 129.5 (CH), 129.0 (CH), 128.7 (C), 127.8 (CH), 127.5 (CH), 127.2 (CH), 127.0 (CH), 125.7 (CH), 125.0 (CH), 123.2 (C), 123.0 (CH), 121.9 (CH), 121.1 (C), 120.5 (CH), 42.2 (CH$_2$), 29.7 (CH$_2$). Mass spectrum m/z 365 (6) [(M–Pd(PPh$_3$)$_2$Br+H)$^{+\cdot}$]; 277 (26); 272 (32) {[M–C$_6$H$_4$OPd(PPh$_3$)$_2$Br$^+$]}; 262 (100) (Ph$_3$P$^{+\cdot}$).

1-Phenylpyrrolo[2,1-a]isoquinoline (18) and 1-[2'-(2"-Bromophenyl)ethyl]-4-phenylpyrrole (19)

A solution of the dibromide (4) (13 mg, 25 mmol), trans-di(m-acetato)-bis[o-(di-o-tolylphosphino)benzyl]dipalladium(II) Chem., Eur. J., 1997, 3, 1357, (2.5 mg, 2.5 mmol) and anhydrous sodium acetate (6.2 mg, 75 mmol) in degassed N,N-dimethylacetamide (0.25 ml) was heated, under nitrogen, at 140° C. for 72 h. The cooled reaction mixture was then diluted with diethyl ether (5 ml) and the resulting solution washed with brine/water (3×5 ml of a 1:1 v/v mixture). The organic phase was then dried (MgSO$_4$), filtered and concentrated under reduced pressure to give a light-yellow oil. Subjection of this material to flash chromatography (silica, 3:7 then 7:3 CH$_2$Cl$_2$/hexane elution) gave, after concentration of the appropriate fractions (R$_f$ 0.7, 3:7 CH$_2$Cl$_2$/hexane elution), a 1:3 mixture of compounds (18) and (19) (4 mg, 52% combined yield) as a light-yellow and unstable oil. n$_{max}$ (KBr) 1705, 41.2, 1555, 1500, 1471, 1441, 1359, 1202, 1071, 1027, 751, 694, 655 cm$^{-1}$. $^1$H n.m.r. d [compound (18)] 7.60–6.95, complex m, 9H; 6.92, t, J 2.0 Hz, 1H, H-2; 6.63, t, J 1.6 Hz, 1H, H-5; 6.43, broadened t, J 2.3 Hz, 1H, H4; 4.14, t, J 7.7 Hz, 2H; 3.22, t, J 7.7 Hz, 2H; [compound (19)] 7.60–6.95, complex m, 9H; 6.73, d, J 2.7 Hz, 1H, H-3; 6.23, d, J 2.7 Hz, 1H, H-2; 4.08, t, J 7.7 Hz, 2H; 3.10, t, J 7.7 Hz, 2H. G.P./Ms. [compound (18)] (R$_f$ 4.52 min.) 245 (100) (M$^{+\cdot}$), 246 (100) (21), 149 (28), 120 (6); [compound (19)] (R$_f$ 5.85 min.) 327 (12) 325 (12) (M$^{+\cdot}$), 167 [(M–Br$^\cdot$)$^+$].

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A method for the preparation of a compound of Formula (II)

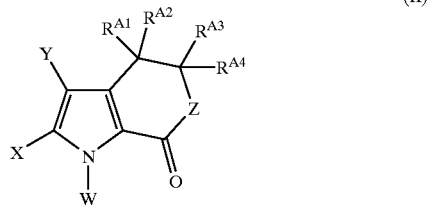

(II)

comprising the step of performing an intramolecular cyclization of a compound of Formula

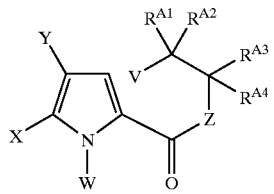

(I)

wherein:

$R^{A1-A4}$ are each independently selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano; or $R^{A2}$ and $R^{A3}$ may optionally together form a bond and $R^{A1}$ and $R^{A4}$ are as defined above or together with the carbon atoms to which they are attached form an optionally substituted carbocyclic or heterocyclic group; or $R^{A2}$ and $R^{A3}$, together with the carbon atoms to which they are attached form an optionally substituted saturated or unsaturated carbocyclic or heterocyclic group; or $R^{A1}R^{A2}C$—$CR^{A3}R^{A4}$ forms an optionally substituted aryl group or aromatic heterocyclic group;

Y is selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano;

W and X are as defined for Y, or together with the nitrogen and carbon atoms to which they are attached, form a saturated or unsaturated nitrogen containing heterocyclic group which may be optionally substituted or optionally fused to a saturated or unsaturated carbocyclic group, aryl group or heterocyclic group;

V represents a halogen or hydrogen atom;

Z is —$(CH_2)n$—U—$(CH_2)_o$— where U is selected from $CH_2$, NH or a heteroatom, and n and o are independently selected from 0, 1, 2 or 3.

2. A method according to claim 1 wherein W and X together with the nitrogen and carbon atoms to which they are attached, form a saturated or unsaturated nitrogen containing heterocyclic group which may be optionally substituted or optionally fused to a saturated or unsaturated carbocyclic group, aryl group or heterocyclic group.

3. A method according to claim 2 wherein W and X, together with the nitrogen and carbon atoms to which they are attached, form a group selected from an optionally substituted quinolinyl group, optionally substituted isoquinolinyl group, optionally substituted dihydroquinolinyl group, optionally substituted dihydroisoquinolinyl group, optionally substituted pyridyl group or dihydro or tetrahydro congeners thereof, or optionally substituted phenanthridine.

4. A method according to claim 3 wherein W and X together with the nitrogen and carbon atoms to which they are attached, form an optionally substituted isoquinolinyl or optionally substituted dihydroisoquinolinyl group of general Formula (i):

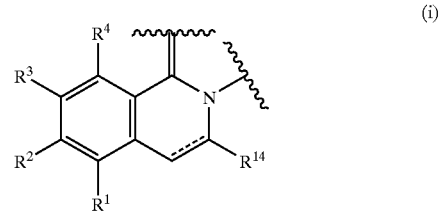

(i)

wherein $R^1$–$R^4$ and $R^{14}$ are selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano, and represents an optional double bond.

5. A method according to claim 4 wherein $R^1$–$R^4$ are independent selected from the group consisting of hydrogen; hydroxy; optionally substituted alkyl; optionally substituted alkyloxy; acyloxy; carboxy; carboxy ester; optionally substituted amino; carboxamido; or sulfate; and $R^{14}$ is hydrogen or hydroxy.

6. A method for the preparation of a compound of Formula (IIa):

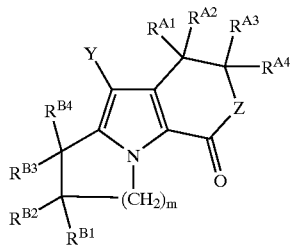

(IIa)

comprsing the step of performing two intramolecular cyclizations on a compound of Formula (Ia):

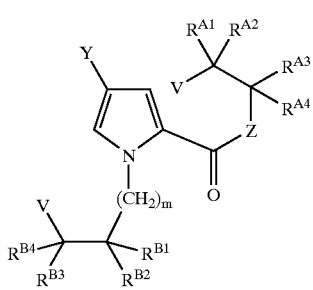

(Ia)

wherein:

$R^{A1-A4}$, V, Y, Z are as defined in claim 1;

$R^{B1-B4}$ are each independently selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano; or $R^{B2}$ and $R^{B3}$ may optionally together form a bond and $R^{A1}$ and $R^{A4}$ are as defined above or together with the carbon atoms to which they are attached form an optionally substituted carbocyclic or heterocyclic group; or $R^{B2}$ and $R^{B3}$, together with the carbon atoms to which they are attached form an optionally substituted saturated or unsaturated carbocyclic or heterocyclic group; or $R^{B1}R^{B2}C$—$CR^{B3}R^{B4}$ form an optionally substituted aryl group or aromatic heterocyclic group; and m is selected from 1, 2, 3 or 4.

7. A method according to claim 6 wherein m is 1 or 2, preferably 2.

8. A method according to claim 1 wherein $R^{A1}R^{A2}C$—$CR^{A3}R^{A4}$ forms an aryl group or an aromatic heterocyclic group, said group selected from: an optionally substituted benzene or naphthalene ring or an optionally substituted pyridine, optionally substituted furan, optionally substituted pyrrole or optionally substituted thiophene and benzene-fused analogues thereof.

9. A method according to claim 8 wherein $R^{A1}R^{A2}C$—$CR^{A3}R^{A4}$ forms an optionally substituted benzene group.

10. A method according to claim 9 wherein the substituents are selected from: hydrogen; hydroxy; optionally substituted alkyl; optionally substituted alkyloxy; acyloxy; carboxy; carboxy ester; optionally substituted amino; carboxamido; or sulfate.

11. A method according to claim 1 wherein Y is an optionally substituted phenyl group of Formula (ii):

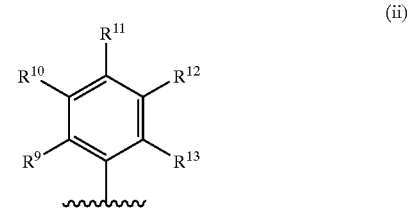

(ii)

wherein $R^9$–$R^{13}$ are selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano.

12. A method according to claim 11 wherein $R^9$–$R^{13}$ are independently selected from hydrogen; hydroxy; optionally substituted alkyl; optionally substituted alkyloxy; acyloxy; carboxy; carboxy ester; optionally substituted amino; carboxamido; or sulfate.

13. A method according to claim 10 wherein $R^9$–$R^{13}$ are independently selected from hydrogen, hydroxy, methoxy, ethoxy, iso-propoxy, methyl, ethyl, n-propyl, isopropyl, acetoxy or sulphate.

14. A method of preparing a fused polycyclic pyrrole-containing compound of Formula (IIb):

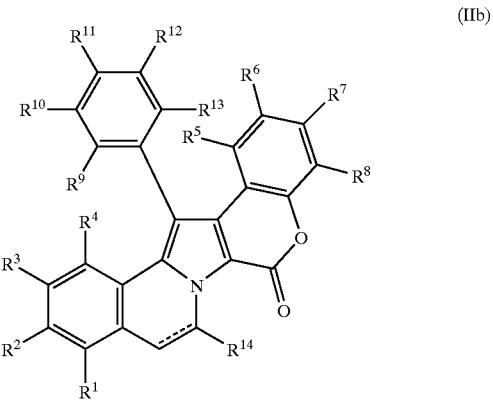

(IIb)

comprising the step of performing two intramolecular cyclizations on a compound of Formula (Ib):

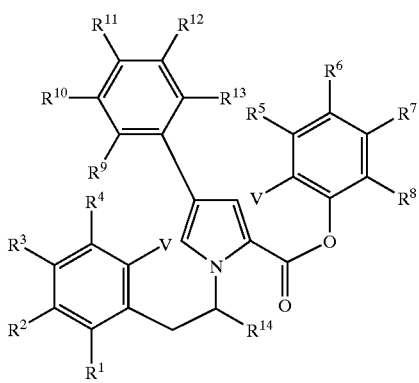

(Ib)

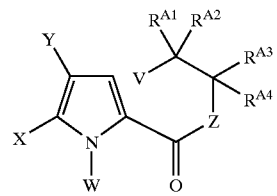

(I)

wherein V is halogen or hydrogen and $R^1$–$R^{14}$ are independently selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano; and optionally dehydrogenating the cyclized product to form a compound of Formula (Ib) wherein the optional double bond ==== is present.

15. A method according to claim 14 wherein $R^1$–$R^{14}$ are independently selected from: hydrogen; hydroxy; optionally substituted alkyl; optionally substituted alkyloxy; acyloxy; carboxy; carboxy ester; optionally substituted amino; carboxamido; or sulfate, preferably $R^1$–$R^{13}$ are independently selected from hydrogen; hydroxy; optionally substituted alkyl, such as methyl, ethyl or propyl; optionally substituted alkyloxy such as methoxy, ethoxy, n-propoxy, iso-propoxy; acyloxy such as acetoxy; or sulfate and $R^{14}$ is preferably hydrogen or hydroxy and V is bromine, iodine or hydrogen.

16. A method according to claim 1 wherein U, as defined in Z, is selected from one of $CH_2$, NH or oxygen, preferably oxygen, and n+o=0, 1, 2, 3 or 4, preferably 0.

17. A method according to claim 1 wherein each V is independently hydrogen, bromine or iodine.

18. A method according to claim 1 wherein V is hydrogen, and the cyclization occurs under oxidative conditions.

19. A method according to claim 1 wherein V is a halogen atom, preferably bromine or iodine, and the cyclization occurs via the the generation of a radical of Formula (I).

20. A method according to claim 1 wherein V is a halogen atom, preferably bromine or iodine, and the cyclization occurs via a Pd[0]-catalyzed process.

21. A method according to claim 6 wherein both V are halogen, preferably bromine or iodine, and the two cyclizations are performed in one pot.

22. A method according to claim 21 wherein the one pot double cyclization is Pd[0]-catalyzed.

23. A compound of Formula (I)

wherein:

$R^{A1-A4}$ are each independently selected from hydrogen, optionally substituted alkyl, optionally substituted alkenyl, optionally substituted alkynyl, optionally protected hydroxy, optionally substituted amino, optionally substituted alkoyx, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano; or $R^{A2}$ and $R^{A3}$ may optionally together form a bond and $R^{A1}$ and $R^{A4}$ are as defined above or together with the carbon atoms to which they are attached form an optionally substituted carbocyclic or heterocyclic group; or $R^{A2}$ and $R^{A3}$, together with the carbon atoms to which they are attached form an optionally substituted saturated or unsaturated carbocyclic or heterocyclic group; or $R^{A1}R^{A2}C$—$CR^{A3}R^{A4}$ forms an optionally substituted aryl group or aromatic heterocyclic group;

Y is selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano;

W and X, together with the nitrogen and carbon atoms to which they are attached, form a saturated or unsaturated nitrogen containing heterocyclic group which may be optionally substituted or optionally fused to a saturated or unsaturated carbocyclic group, aryl group, or heterocyclic group;

V represents a halogen or hydrogen atom;

Z is —$(CH_2)_n$—U—$(CH_2)_o$— where U is selected from $CH_2$, NH or a heteroatom, and n and o are independently selected from 0, 1, 2 or 3.

24. A compound of Formula (Ia):

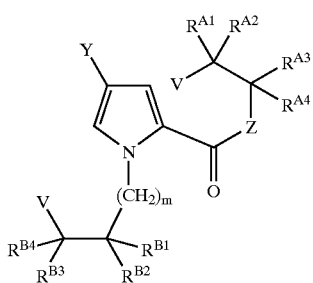

(Ia)

wherein:

- $R^{A1-A4}$ are each independently selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano; or
- $R^{A2}$ and $R^{A3}$ optionally together form a bond and $R^{A1}$ and $R^{A4}$ are as defined above or together with the carbon atoms to which they are attached form an optionally substituted saturated or unsaturated carbocyclic or heterocyclic group; or
- $R^{A2}$ and $R^{A3}$, together with the carbon atoms to which they are attached form an optionally substituted saturated or unsaturated carbocyclic or heterocyclic group; or
- $R^{A1}R^{A2}C-CR^{A3}R^{A4}$ forms an optionally substituted aryl group or aromatic heterocyclic group;
- $R^{B1-B4}$ are each independently selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano;
- $R^{B2}$ and $R^{B3}$ may optionally together form a bond and $R^{A1}$ and $R^{A4}$ are as defined above or together with the carbon atoms to which they are attached form an optionally substituted carbocyclic or heterocyclic group; or
- $R^{B2}$ and $R^{B3}$, together with the carbon atoms to which they are attached form an optionally substituted saturated or unsaturated carbocyclic or heterocyclic group: or
- $R^{B1}R^{B2}C-CR^{B3}R^{B4}$ form an optionally substituted aryl group or aromatic heterocyclic group;
- Y is selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano;
- V represents a halogen or hydrogen atom; and
- Z is $-(CH_2)_n-U-(CH_2)_o-$ where U is selected from $CH_2$, NH or a heteroatom, and n and o are independently selected from 0, 1, 2 or 3; and
- m is selected from 1, 2, and 3.

25. A compound according to claim 23 or 24 wherein $R^{A1}R^{A2}C-CR^{A3}R^{A4}$ forms an optionally substituted benzene group.

26. A compound of Formula (Ib):

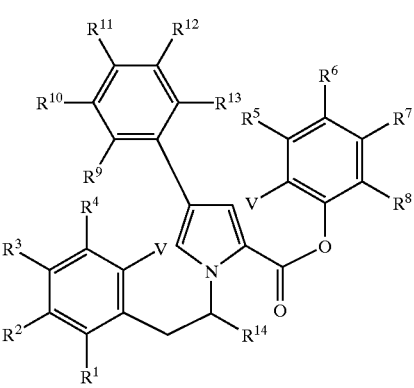

(Ib)

wherein

- $R^{1-14}$ are independently selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano; and
- V is halogen or hydrogen.

27. A compound according to claim 26 wherein $R^1-R^{14}$ are independently selected from: hydrogen; hydroxy; optionally substituted alkyl; optionally substituted alkyloxy; acyloxy; carboxy; carboxy ester; optionally substituted amino; carboxamido; or sulfate, preferably $R^1-R^{13}$ are independently selected from hydrogen; hydroxy; optionally substituted alkyl, such as methyl, ethyl or propyl; optionally substituted alkyloxy such as methoxy, ethoxy, n-propoxy, iso-propoxy; acyloxy such as acetoxy; or sulfate and $R^{14}$ is preferably hydrogen or hydroxy; and V is bromine, iodine or hydrogen.

28. A method of preparing fused polycyclic pyrrole-containing compounds comprising the step of performing two intramolecular cyclizations on a compound of Formula (Ib):

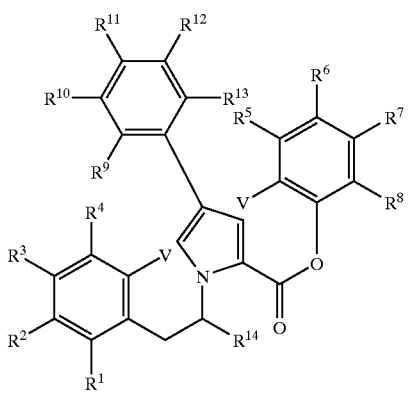

Formula Ib wherein V is halogen or hydrogen and $R^1$–$R^{14}$ are independently selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano.

* * * * *

UNITED STATES PATENT AND TRADEMARK OFFICE
CERTIFICATE OF CORRECTION

PATENT NO. : 6,469,171 B1
DATED : October 22, 2002
INVENTOR(S) : Banwell et al.

It is certified that error appears in the above-identified patent and that said Letters Patent is hereby corrected as shown below:

Column 1,
Line 27, replace "are, isolated" with -- are isolated --.
Line 54, add -- ; -- after "2259)".

Column 2,
Line 12, add -- of -- after "step".

Column 5,
Lines 22, 28, 31, 35 and 39, replace "group" with -- groups --.

Column 7,
Line 66, replace "amin" with -- amine --.

Column 9,
Line 61, replace "in" with -- m --.

Column 10,
Line 31, replace "amin" with -- amine --.
Line 35, replace "$R^{A1}$" with -- $R^{B1}$ --.
Line 35, replace "$R^{A4}$" with -- $R^{B4}$ --.

Column 11,
Line 44, replace "Ia" with -- IIa --.

Column 12,
Line 28, replace "Ia" with -- IIa --.
Line 28, replace "the-same" with -- the same --.

Column 13,
Line 55, replace "$CH_2C_2$" with -- $CH_2Cl_2$ --.
Line 61, delete "$0^{®}$".

Column 14,
Line 53, replace "benzoqionone" with -- benzoquinone --.

UNITED STATES PATENT AND TRADEMARK OFFICE
CERTIFICATE OF CORRECTION

PATENT NO. : 6,469,171 B1
DATED : October 22, 2002
INVENTOR(S) : Banwell et al.

It is certified that error appears in the above-identified patent and that said Letters Patent is hereby corrected as shown below:

Column 18,
Table 2, delete "$R^{12}$" in the 10$^{th}$ column, first row and insert -- $R^{12}$ -- in the 11$^{th}$ column, first row.

Column 19,
Table 2, delete "$R^{12}$" in the 10$^{th}$ column, first row and insert -- $R^{12}$ -- in the 11$^{th}$ column, first row.

Column 21,
Line 11, delete ".".
Lines 17 and 43, replace "$n_{max}$" with -- $v_{max}$ --.
Line 25, replace "$\cdot]\cdot$" with -- $\cdot]$ --.

Column 22,
Line 9, replace "$n_{max}$" with -- $v_{max}$ --.
Line 36, replace "$C_{19}H_4$" with -- $C_{19}H_{14}$ --.
Line 37, replace "$n_{max}$" with -- $v_{max}$ -- and insert -- C, 39.7; H -- after "requires".
Line 41, replace "7.55, dd,J2H;" with -- 4.55, t, J7.5Hz, 2H; --.
Line 63, replace "$(MgS_40)$" with -- $(MgSO_4)$ --.

Column 23,
Line 3, replace "$m_{max}$" with -- $v_{max}$ --.
Line 4, replace "$cm^{31}$" with -- $cm^{-1}$ --.
Line 13, replace "Bro" with -- BrO --.
Line 16, replace "-6one" with -- 6-one --.
Lines 33 and 67, replace "$n_{max}$" with -- $v_{max}$ --.
Line 39, replace "13C" with -- $^{13}C$ --.

Column 24,
Lines 13 and 45, replace "$n_{max}$" with -- $v_{max}$ --.
Line 48, replace "H4" with -- H-4 --.
Line 52, replace "G.P./Ms." with -- G.c./M.S. --.
Lines 52 and 54, replace "$R_f$" with -- $R_t$ --.
Line 54, replace ", 167" with -- 246 (100) --.

UNITED STATES PATENT AND TRADEMARK OFFICE
CERTIFICATE OF CORRECTION

PATENT NO. : 6,469,171 B1
DATED : October 22, 2002
INVENTOR(S) : Banwell et al.

It is certified that error appears in the above-identified patent and that said Letters Patent is hereby corrected as shown below:

Column 26,
Line 8, replace "(CH$_2$)n" with -- (CH$_2$)$_n$ --.
Line 55, insert -- ------- -- before "represents".
Line 59, replace "independent" with -- independently --.

Column 29,
Line 30, replace "(Ib)" with -- (IIb) --.

Signed and Sealed this

Twenty-first Day of October, 2003

JAMES E. ROGAN
*Director of the United States Patent and Trademark Office*